United States Patent [19]

Nakamatsu et al.

[11] Patent Number: 5,599,971
[45] Date of Patent: Feb. 4, 1997

[54] METHOD FOR PRODUCING 1,4-DIHYDROXY-2-NAPHTHOIC ACID

[75] Inventors: Toshio Nakamatsu; Yasuhiro Nishida, both of Hyogo; Shinichi Watanabe, Kyoto; Norio Kometani, Osaka, all of Japan

[73] Assignees: Sumitomo Chemical Company, Limited; Sumika Fine Chemicals Co., Ltd., both of Osaka, Japan

[21] Appl. No.: 383,688

[22] Filed: Feb. 1, 1995

Related U.S. Application Data

[63] Continuation of Ser. No. 5,080, Jan. 15, 1993, abandoned.

[30] Foreign Application Priority Data

Jan. 17, 1992 [JP] Japan ................... 4-006340

[51] Int. Cl.⁶ .................................................. C07C 51/15
[52] U.S. Cl. ............................................................ 562/425
[58] Field of Search ................................. 562/424, 425

[56] References Cited

U.S. PATENT DOCUMENTS

| | | | |
|---|---|---|---|
| 1,697,332 | 1/1929 | Stenzl | 562/425 |
| 2,807,643 | 9/1957 | Hartley | 562/425 |
| 3,825,593 | 7/1974 | Meek | 562/424 |

FOREIGN PATENT DOCUMENTS

| | | | |
|---|---|---|---|
| 0436379 | 7/1991 | European Pat. Off. | |
| 1046628 | 12/1958 | Germany. | |
| 57-128655 | 8/1982 | Japan. | |
| 57-126443 | 8/1982 | Japan | 562/425 |
| 59-141537 | 8/1984 | Japan. | |
| 60-104037 | 6/1985 | Japan. | |
| 734622 | 8/1955 | United Kingdom. | |

OTHER PUBLICATIONS

Lindsey, Chem. Rev., 57, pp. 583–620 (1957).
Homeyer et al, "A Study of Diethyl 1,4–Dihydroxy–2, 3–Naphthalate," J. Am. Chem. Soc., vol. 64, p. 798, Apr. 1942.
J. Prakt. Chem., vol. 62, No. 2, p. 30, May 1900.

*Primary Examiner*—Michael L. Shippen
*Attorney, Agent, or Firm*—Sughrue, Mion, Zinn, Macpeak & Seas

[57] ABSTRACT

A method for producing 1,4-dihydroxy-2-naphthoic acid which comprises the steps of: subjecting 1,4-dihydroxynaphthalene into an alkali metal salt formation reaction in an organic medium capable of dissolving 1,4-dihydroxynaphthalene using an alkali metal alcoholate; and subjecting the salt formation reaction mixture to carboxylation using carbon dioxide gas.

9 Claims, No Drawings

METHOD FOR PRODUCING 1,4-DIHYDROXY-2-NAPHTHOIC ACID

This is a Continuation of application No. 08/005,080 filed Jan. 15, 1993 (now abandoned).

FIELD OF THE INVENTION

This invention relates to a method for producing 1,4-dihydroxy-2-naphthoic acid.

BACKGROUND OF THE INVENTION

There has been proposed several methods for producing 1,4-dihydroxy-2-naphthoic acid which is useful as an intermediate in the production of dyes, pigments and photographic agents.

For example, *J. Am. Chem. Soc.*, vol. 64, 798 (1942) reports a method for producing 1,4-dihydroxy-2-naphthoic acid by using phthalic acid and a succinate. *J. Prakt. Chem.*, vol. (2)62, p. 30 (1900) reports that the target naphthoic acid is synthesized by reacting 1,4-dihydroxynaphthalene with alcoholic sodium hydroxide or alcoholic potassium hydroxide in an alcohol solvent to form a sodium or potassium salt thereof, drying the obtained product in a hydrogen gas stream, allowing the crystals thus obtained to reaction with carbon dioxide under increased pressure of carbon dioxide gas at 170° C. for 20 to 30 hours, and then subjecting the reaction mixture to salting out with diluted hydrochloride acid.

In recent years, JP-A-57-126443 and JP-A-57-128655 propose each a method for carboxylating 1,4-dihydroxynaphthalene with carbon dioxide gas in an organic medium in the presence of potassium carbonate anhydride in the form of fine particles. JP-A-59-141537 and JP-A-60-104037 also propose each a method for carboxylating 1,4-dihydroxynaphthalene with carbon dioxide gas in the presence of an alkali metal compound and water. The term "JP-A" as used herein means an "unexamined published Japanese patent application".

However, the method for producing 1,4-dihydroxy-2-naphthoic acid from phthalic acid and a succinate requires a long time and a complicated procedure. In the case of the method comprising isolating an alkali metal salt of 1,4-dihydroxynaphthalene and then carboxylating with carbon dioxide gas, the alkali metal salt of 1,4-dihydroxynaphthalene is highly unstable and a large amount of by-products are formed, thereby decreasing the yield of the desired product. In addition, there are a number of difficulties in the embodiment of this method on an industrial scale.

In the case of the methods described in JP-A-57-126443 and JP-A-57-128655, it is necessary to use highly hygroscopic fine particles of potassium carbonate anhydride and to carry out the reaction at a high temperature under an increased pressure for a long period of time while maintaining the moisture content at a level of 0.5% or less. In addition, a complicated procedure is needed in order to isolate the desired 1,4-dihydroxy-2-naphthoic acid from the reaction mixture.

The methods described in JP-A-59-141537 and JP-A-60-104037 can establish only a low conversion ratio and it is therefore needed to recover the starting material. In addition, it is necessary to rapidly cool the reaction mixture after the completion of the reaction, since the cooling rate affects the yield.

Thus, although there have been proposed several methods for producing 1,4-dihydroxy-2-naphthoic acid, it is hard to say that they are advantageous from an industrial viewpoint. Therefore, it has been urgently required to establish an industrially advantageous method for producing 1,4-dihydroxy-2-naphthoic acid.

SUMMARY OF THE INVENTION

The present inventors have conducted extensive studies to establish a method for producing 1,4-dihydroxy-2-naphthoic acid industrially easily and advantageously at a high yield. As a result, the present inventors have successfully found out that 1,4-dihydroxynaphthalene can be industrially easily converted into an alkali metal salt thereof by the reaction with an alkali metal alcoholate in an organic medium capable of dissolving 1,4-dihydroxynaphthalene, and that the metal salt without isolation can be easily and quantitatively carboxylated with carbon dioxide gas in that organic medium.

An object of the present invention is to provide a method for producing 1,4-dihydroxy-2-naphthoic acid industrially easily and advantageously at a high yield.

Other objects and effects of the present invention will be apparent from the following description.

The present invention provides a method for producing 1,4-dihydroxy-2-naphthoic acid, which comprises the steps of: subjecting 1,4-dihydroxynaphthalene to alkali metal salt formation reaction in an organic medium capable of dissolving 1,4-dihydroxynaphthalene using an alkali metal alcoholate; and subjecting the salt formation reaction mixture to carboxylation using carbon dioxide gas.

DETAILED DESCRIPTION OF THE INVENTION

Examples of the organic medium capable of dissolving 1,4-dihydroxynaphthalene used in the present invention include ketones, esters, monoalcohols, polyhydric alcohols and derivatives thereof such as alkyl ethers, and aromatic hydrocarbons. Among these materials, those having a boiling point of 130° C. or more are preferred, and monoalcohols, polyhydric alcohols and derivatives thereof having a boiling point of 130° C. or more are particularly preferred. It is the most preferred to use monoalcohols, polyhydric alcohols and derivatives thereof having a boiling point of 130° C. or more and a solubility parameter $\delta$ of 13 or less.

Specific examples of the organic medium include dipropylene glycol, dipropylene glycol monomethyl ether, diethylene glycol monomethyl ether, ethylene glycol monobutyl ether, hexylene glycol, and octanol.

The organic medium is generally used in an amount from 1 to 20 times by weight, preferably from 3 to 10 times by weight, the weight of the 1,4-dihydroxynaphthalene.

As the alkali metal alcoholate, alcoholates of alcohols having from 1 to 4 carbon atoms may be used. From an industrial viewpoint, it is preferred to use less expensive ones such as sodium methylate and sodium ethylate.

The alkali metal alcoholate is generally used in an amount of 1.5 mols or more, preferably from 2 to 3 mols, more preferably from 2.0 to 2.4 mols, per mol of the 1,4-dihydroxynaphthalene.

The alkali metal salt formation reaction is preferably carried out at a temperature of 110° C. or more, more preferably from 150° to 180° C.

The salt formation reaction is carried out while removing the lower alcohol formed during the reaction out of the reaction systems. The lower alcohol may be removed in a conventional manner such as, for example, distillation under reduced pressure. It is preferred to perform the removal of lower alcohol by substitution of the atmosphere with an inert gas such as nitrogen gas or bubbing the inert gas into the reaction mixture.

According to the salt formation reaction of the present invention, even if the organic medium and/or the starting materials contain any moisture, adverse effects can be avoided because the reaction temperature is relatively high as mentioned above. It is preferred, however, to control the moisture content in the reaction mixture to 3% by weight or less.

In the present invention, the alkali metal salt of 1,4-dihydroxynaphthalene is subjected to subsequent carboxylation without isolation from the reaction mixture. The carboxylation is performed by blowing carbon dioxide gas into the salt formation reaction mixture.

The carbon dioxide gas may be used in a stoichiometric amount, preferably in an excess amount such as 1.5 mols or more per mol of 1,4-dihydroxynaphthalene.

The carboxylation reaction temperature may preferably range from 50° to 180° C., more preferably from 90° to 130° C., by taking the stability of the desired product and the reaction ratio into consideration.

Although this carboxylation reaction may be carried out under atmospheric pressure, it may be performed under an increased pressure, if needed. In the latter case, the pressure may be approximately 10 kg/cm$^2$ or less.

After the reaction is over, the desired 1,4-dihydroxy-2-naphthoic acid thus obtained may be isolated in a conventional manner. For example, the reaction mixture is desirably cooled, then diluted with a poor solvent such as water, neutralized with an acid and desirably filtered, followed by precipitation using an acid, filteration and washing with water. Thus 1,4-dihydroxy-2-naphthoic acid of a high purity can be obtained.

In the above isolation procedure, the neutralization of the reaction mixture may be carried out prior to the dilution using the poor solvent such as water.

The acid used for the neutralization and the acid-precipitation may be selected from organic acids such as acetic acid, and mineral acids such as hydrochloric acid and sulfuric acid. These acids may be used singly or in combination of two or more of them. The pH value at the neutralization may preferably range from 4 to 6, more preferably from 4.5 to 5.5. The pH value at the acid-precipitation may be preferably around 1.

The amount of the water to be used for the dilution may be preferably from 1 to 10 times by weight, more preferably from 3 to 5 times by weight, the weight of the organic medium employed.

According to the present invention, 1,4-dihydroxy-2-naphthoic acid of a high purity can be industrially easily and advantageously obtained at a high yield.

The present invention will be described in more detail by referring to the following examples, but the present invention is not construed as being limited thereto. All parts, percents and the like referred in the following examples are by weight unless otherwise indicated.

In the following Examples, the purity of the product was determined by a known neutralization titration method for carboxylic acids.

EXAMPLE 1

16 Parts of 1,4-dihydroxynaphthalene was added to 100 parts of dipropylene glycol monomethyl ether in a reaction vessel provided with a stirrer under a nitrogen atmosphere at room temperature. 42.5 Parts of 28% sodium methylate was added dropwise thereto. Then the reaction mixture was heated to 180° C. and maintained at this temperature for 1 hour. During this period, 36 parts of a distillate mainly composed of methanol was removed out of the reaction system. After cooling to 110° C., carbon dioxide gas was blown into the reaction mixture under atmospheric pressure. Although the absorption of the carbon dioxide gas was completed within 15 minutes, carbon dioxide gas was further blown for additional 15 minutes.

1,4-Dihydroxy-2-naphthoic acid produced in the reaction mixture was isolated in the following manner: The reaction atmosphere was substituted with nitrogen gas and cooled to 60° C., and 30 parts of a 67% aqueous solution of acetic acid was added dropwise thereto. The reaction mixture was discharged into 45 parts of warm water. After confirming that the pH value was 4.8, the insoluble matters thus formed were filtered, 35% hydrochloric acid was added to the filtrate to adjust the mixture to pH 1.0. After cooling, the precipitate thus formed was filtered, washed with water and dried. Thus 18.6 parts of 1,4-dihydroxy-2-naphthoic acid was obtained in the form of crystals. The purity of this product was 98.8% and the yield thereof was 92.3%.

EXAMPLES 2 TO 5

The procedure of the above Example 1 was repeated except that the blowing temperature of the carbon dioxide gas was changed as shown in Table 1. Table 1 summarizes the results.

TABLE 1

| Example | CO$_2$ gas blowing temperature (°C.) | 1,4-dihydroxy-2-naphthoic acid Purity (%) | Yield (%) |
| --- | --- | --- | --- |
| 2 | 130 | 97.5 | 87.0 |
| 3 | 160 | 95.4 | 81.0 |
| 4 | 90 | 98.3 | 88.6 |
| 5 | 170 | 94.8 | 77.8 |

EXAMPLE 6

The procedure of the above Example 1 was repeated except that the dipropylene glycol monomethyl ether employed as the reaction medium was replaced with 100 parts of diethylene glycol monomethyl ether. As a result, 18.5 parts of 1,4-dihydroxy-2-naphthoic acid was obtained in the form of crystals. The purity of this product was 98.1% and the yield thereof was 89.2%.

EXAMPLE 7

The procedure of the above Example 1 was repeated except that the dipropylene glycol monomethyl ether employed as the reaction medium was replaced with 100 parts of hexylene glycol. As a result, 17.6 parts of 1,4-dihydroxy-2-naphthoic acid was obtained in the form of crystals. The purity of this product Was 98.4% and the yield thereof was 85.0%.

EXAMPLE 8

The procedure of the above Example 1 was repeated except that the 28% sodium methylate was used in an amount of 63.8 parts and that 27 parts of acetic acid was employed for the neutralization. As a result, 18.7 parts of 1,4-dihydroxy-2-naphthoic acid was obtained in the form of crystals. The purity of this product was 96.4% and the yield thereof was 88.7%.

EXAMPLE 9

32 Parts of 1,4-dihydroxynaphthalene was added to 200 parts of dipropylene glycol monomethyl ether in a pressure reaction vessel provided with a stirrer under nitrogen atmosphere at room temperature. 85 Parts of 28% sodium methylate was added dropwise thereto. Then the reaction mixture was heated to 180° C. and maintained at this temperature for 1 hour. During this period, 62 parts of a distillate mainly composed of methanol was formed. After cooling to 110° C., carbon dioxide gas was pressed into the reaction mixture and the mixture was reacted for 1 hour while maintaining the pressure at 5 kg/cm$^2$ with feeding carbon dioxide gas thereto.

After the reaction was over, the pressure was relieved and 1,4-dihydroxy-2-naphthoic acid was isolated in the same manner as in Example 1. Thus 37.3 parts of 1,4-dihydroxy-2-naphthoic acid was obtained in the form of crystals. The purity of this product was 97.9% and the yield thereof was 89.4%.

EXAMPLES 10 TO 12

The procedure of the above Example 1 was repeated except that the temperature for distilling off methanol and maintaining thereafter was changed as shown in Table 2. Table 2 summarizes the results.

TABLE 2

| Example | Methanol distillation temperature (°C.) | 1,4-dihydroxy-2-naphthoic acid Purity (%) | Yield (%) |
|---|---|---|---|
| 10 | 150 | 96.0 | 80.5 |
| 11 | 160 | 95.4 | 84.7 |
| 12 | 170 | 97.9 | 89.2 |

While the invention has been described in detail and with reference to specific examples thereof, it will be apparent to one skilled in the art that various changes and modifications can be made therein without departing from the spirit and scope thereof.

What is claimed is:

1. A method for producing 1,4-dihydroxy-2-naphthoic acid, which comprises the steps of:

subjecting 1,4-dihydroxynaphthalene to an alkali metal salt formation reaction in an organic medium using an alkali metal alcoholate, wherein said organic medium is selected from the group consisting of polyhydric alcohols and polyhydric alcohol alkyl ethers, wherein said polyhydric alcohols and polyhydric alcohol alkyl ethers have a boiling point of 130° C. or more and a solubility parameter δ of 13 or less; and subjecting the salt formation reaction mixture to carboxylation using carbon dioxide gas.

2. A method as claimed in claim 1, wherein said organic medium is used in an amount of from 1 to 20 times by weight of said 1,4-dihydroxynaphthalene.

3. A method as claimed in claim 1, wherein said alkali metal alcoholate is an alcoholate of an alcohol having from 1 to 4 carbon atoms.

4. A method as claimed in claim 1, wherein said alkali metal alcoholate is sodium methylate or sodium ethylate.

5. A method as claimed in claim 1, wherein said alkali metal alcoholate is used in an amount of 1.5 mols or more per mole of said 1,4-dihydroxynaphthalene.

6. A method as claimed in claim 1, wherein the alkali metal salt formation reaction is performed at a temperature of 110° C. or more.

7. A method as claimed in claim 1, wherein the carboxylation is performed under atmospheric pressure or an increased pressure of carbon dioxide gas.

8. A method as claimed in claim 1, wherein the carboxylation is performed at a temperature of from 50° to 180° C.

9. A method as claimed in claim 1, wherein the carboxylation is performed using carbon dioxide in an amount of 1.5 mols or more per mol of said 1,4-dihydroxynaphthalene.

* * * * *